(12) United States Patent
Dutta et al.

(10) Patent No.: US 8,114,675 B2
(45) Date of Patent: Feb. 14, 2012

(54) ROOM TEMPERATURE CO SENSOR AND METHOD OF MAKING SAME

(75) Inventors: Prabir K. Dutta, Worthington, OH (US); Adedunni D. Adeyemo, Silver Spring, MD (US)

(73) Assignee: The Ohio State University Research Foundation, Columbus, OH (US)

( * ) Notice: Subject to any disclaimer, the term of this patent is extended or adjusted under 35 U.S.C. 154(b) by 136 days.

(21) Appl. No.: 12/750,286

(22) Filed: Mar. 30, 2010

(65) Prior Publication Data
US 2010/0255597 A1   Oct. 7, 2010

Related U.S. Application Data

(60) Provisional application No. 61/164,650, filed on Mar. 30, 2009.

(51) Int. Cl.
*G01N 33/00*   (2006.01)
*G01N 27/04*   (2006.01)

(52) U.S. Cl. ............. 436/134; 422/88; 422/90; 422/98; 436/133; 436/151

(58) Field of Classification Search .............. 422/83, 422/88, 90, 94, 98; 436/127, 133–134, 149, 436/151
See application file for complete search history.

(56) References Cited

U.S. PATENT DOCUMENTS

| | | | |
|---|---|---|---|
| 4,579,751 A * | 4/1986 | Forster | 427/595 |
| 4,953,387 A * | 9/1990 | Johnson et al. | 73/25.03 |
| 5,589,046 A | 12/1996 | Li et al. | |
| 5,650,054 A | 7/1997 | Shen et al. | |
| 6,550,310 B1 | 4/2003 | Liu et al. | |
| 6,837,987 B1 | 1/2005 | King | |
| 7,247,592 B2 * | 7/2007 | Echigo et al. | 502/53 |
| 7,694,547 B2 * | 4/2010 | Dutta et al. | 73/23.2 |
| 2004/0038093 A1 * | 2/2004 | Echigo et al. | 429/17 |

OTHER PUBLICATIONS

Swider, K. E. et al, Chemistry of Materials 1997, 9, 1248-1255.*
Jia, Q., in "Handbook of Thin Film Materials, vol. 4: Semiconductor and Superconductor Thin Films" edited by H.S. Nalwa, 2002, Academic Press, chapter 13, pp. 677-698.*
Impellitteri, C. A. et al, Environmental Science and Technology 2003, 37, 2936-2940.*

(Continued)

*Primary Examiner* — Arlen Soderquist
(74) *Attorney, Agent, or Firm* — Calfee, Halter & Griswold LLP

(57) ABSTRACT

Described are CO sensors, methods for making the CO sensors, and methods for using the CO sensors. An exemplary CO sensor includes a ruthenium oxide present in a form having one or more surfaces, a pair of conductive electrodes operatively connected to a surface of the ruthenium oxide, and an electrical device operatively connected to the pair of conductive electrodes. The gas mixture contacts at least one surface of the ruthenium oxide during operation of the sensor and the electrical device applies a constant potential (or current) and measures a current (or potential) between the pair of conductive electrodes, from which a resistance can be derived as the gas mixture contacts at least one surface of the ruthenium oxide. The ruthenium oxide may have varying levels of hydration. Furthermore, the sensor operates at a temperature range of from about 25° C. to about 300° C., the sensor measures CO within a gas mixture when CO is present at concentrations of from about 1 ppm to about 1,000 ppm, and the sensor can measure CO in the presence of one or more interfering gases.

30 Claims, 7 Drawing Sheets

OTHER PUBLICATIONS

Adeyemo, A. et al, Sensors and Actuators B 2011, 152, 307-315.*

Ren-Jang Wu, et al., Promotive effect of CNT on Co3O4-SnO2 in a semiconductor-type CO sensor working at room temperature, Sensors and Actuators, B 131, 2008, pp. 306-312.

A. Salehi, et al., Room temperature carbon monoxide sensor using ITO/n-GaAs Shottky contact, Sensors and Actuators, B 101, 2004, pp. 394-400.

An Yang, et al., Room temperature gas sensing properties of SnO2/multiwall-carbon-nanotube composite nanofibers, Applied Physic Letters 91, 2007, pp. 133110-1 to 133110-3.

Baoyou Geng, et al., A facile coordination compound precursor route to controlled synthesis of Co3O4 nanostructures and their room-temperature gas sensing properties, Journal of Materials Chemistry, The Royal Society of Chemistry, 2008, pp. 4977-4984.

A. Z. Sadek, et al., A layered surface acoustic wave gas sensor based on a polyaniline/In2O3 nanofibre composite, Nanotechnology, 2006, pp. 4488-4492.

Rangachary Mukundan, et al., A low temperature sensor for the detection of carbon monoxide in hydrogen, Solid State Ionics 175, 2004, pp. 497-501.

Roger J. Mortimer, et al., AC impedance characteristics of solid-state planar electrochemical carbon monoxide sensors with Nafion as solid polymer electrolyte, Electrochimica Acta, 2002, pp. 3383-3387.

Serge Zhuiykov, Carbon monoxide detection at low temperatures by semiconductor sensor with nanostructered Au-doped CoOOH films, Sensors and Actuators B 129, 2008, pp. 431-441.

Alireza Salehi, et al., Characteristics of highly sensitive Au/porous-GaAs Shottky junctions as selective CO and NO gas sensors, Sensors and Actuators B 122, 2007, pp. 69-74.

Kyung-Seok Kang, et al., CO gas sensors operating at room temperature, Journal of Materials Science, 2003, pp. 4319-4323.

S. Radhakrishnan, et al., Conducting polypyrrole modified with ferrocene for applications in carbon monoxide sensors, Sensors and Actuators B 125, 2007, pp. 60-65.

Dongliang Fu, et al., Differentiation of Gas Molecules Using Flexible and All-Carbon Nanotube Devices, The Journal of Physical Chemistry, C, vol. 112, No. 3, 2008, pp. 650-653.

P. D. van der Wal, et al., Extremely stable Nafion based carbon monoxide sensor, Sensors and Actuators, B Chemical, B 35-36, 1996 pp. 119-123.

Huiling Tai, et al., Fabrication and gas sensitivity of polyaniline-titanium dioxide nanocomposite thin film, Sensors and Actuators B 125, 2007, pp. 644-650.

Xiaochen Dong, et al., Heme-Enabled Electrical Detection of Carbon Monoxide at Room Temperature Using Networked Carbon Nanotube Field-Effect Transistors, Chemistry of Materials, vol. 19, No. 25, Dec. 11, 2007, pp. 6059-6061.

C. Chuapradit, et al., Polyaniline/zeolite LTA composites and electrical conductivity response towards CO, Polymer 46, 2005, pp. 947-953.

G. Neri, et al, Preparation, characterization and CO sensing of Au/iron oxide thin films, Journal of Materials Science: Materials in Electronics, 2002, pp. 561-565.

* cited by examiner

10

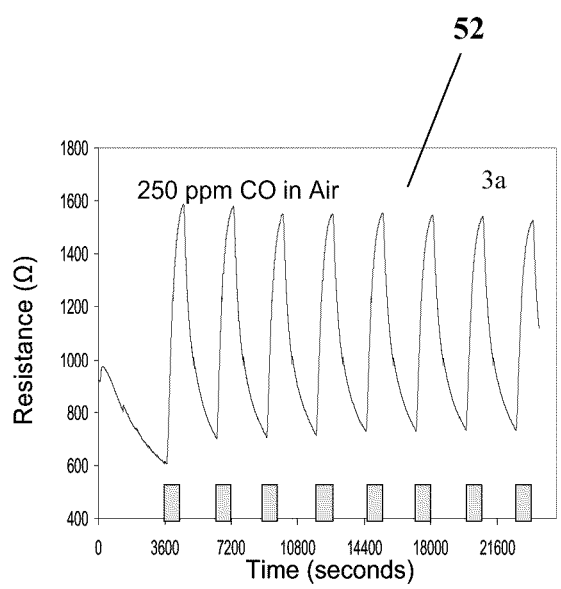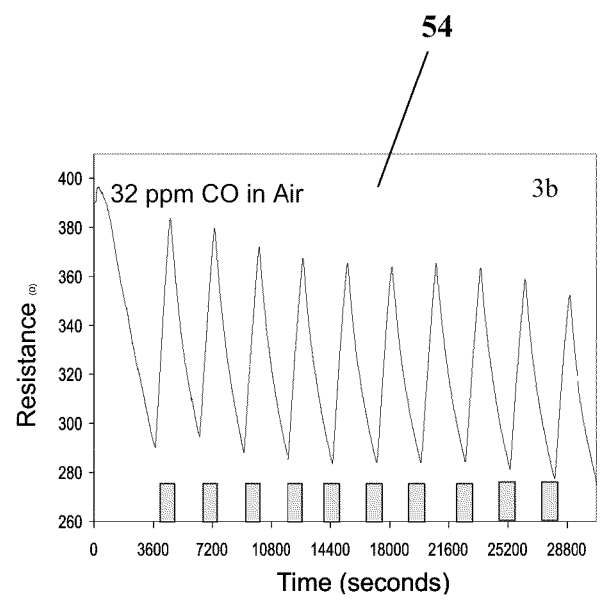
Figure 6A                    Figure 6B

ROOM TEMPERATURE CO SENSOR AND METHOD OF MAKING SAME

This application claims the benefit of U.S. Provisional Application No. 61/164,650, filed Mar. 30, 2009, which is hereby incorporated by reference.

BACKGROUND

1. Field of Invention

The present invention relates to the field of CO sensors and methods of making CO sensors. Specifically, the present invention relates to novel CO sensors made from hydrated metal oxides, and in particular CO sensors made from hydrated ruthenium oxide, which operate at a temperature range of from about 25° C. to about 300° C.

2. Description of Prior Art

Carbon monoxide (CO) is a toxic gas that is one of the major pollutants associated with automotive emissions, combustion processes, fires, manufacturing of natural gas, and a host of other industrial activities. At concentrations higher than 15 ppm, CO is dangerous to the human body. Consequently, reliable, low-cost, CO sensors having high sensitivity, selectivity, and acceptable response and recovery times at low temperatures, and which require low energy consumption are needed for environmental safety and industrial control applications. One of the most basic CO detectors utilizes a chemical compound that changes color in the presence of CO. Although inexpensive, these colormetric CO sensors have high detection thresholds and are not suited for quantitative measurement of varying CO concentrations. Other CO sensing technologies are based on optical or electrochemical detection of CO. Sensors employing optical detection technologies are usually very expensive. Consequently, technologies relying on electrochemical detection of CO are more widely used in conventional CO sensors.

Many different apparatuses can be used in the electrochemical detection and measurement of CO species in a gaseous mixture. Several of these employ either a wet or dry chemical cell to detect and measure CO concentration. For example, certain devices are analogous to fuel cells and operate on principles associated with ionic conduction or charge transfer. Such devices have a basic electrochemical cell configuration and contain two electrodes and an electrolyte (in either a solid or liquid form). The electrochemical cell oxidizes CO at one electrode and reduces oxygen or some other species at the other electrode. A current or voltage related to the amount of CO present is produced, and this can be measured using amperometric or capacitive techniques. Although many types of electrochemical sensors are relatively cheap, reliable, and highly selective to CO detection, many also have a disadvantage in that they are inherently sensitive to a wide range of substances and are susceptible to producing erroneous responses.

Other apparatuses are solid-state devices, which rely on conductive, semiconductor, or a mixture of these two materials to detect and measure CO species electronically. Producing a CO sensor from semiconductor materials is advantageous because such devices can be easily integrated into the design and manufacture of computer chips at low costs. Furthermore, simple electronics can be used to easily monitor the output of such devices using straightforward techniques. Certain devices utilize a semiconductor material and operate on a sensing principle involving chemisorption of CO on the surface of the semiconductor film or substrate. The adsorption of CO on the surface of the semiconductor changes the material's electrical resistance and this change can be measured and calibrated against the concentration of CO that is present.

Several resistive-type CO sensor devices have been constructed from crystalline metal oxide semiconductor (MOS) materials, including, for example, indium oxide, titanium dioxide, and tin oxide. A limitation associated with these MOS materials is that any CO sensor constructed from these materials requires a heating device to operate. This is because the room temperature resistance of these MOS materials are too high for construction of a room temperature CO sensor to be practical. Consequently, heating is required to promote sufficient oxygen vacancies for these MOS materials to be conductive. For example, CO sensors constructed from titanium dioxide require elevated temperatures of up to 350° C. or higher for optimum operation. Unfortunately, the elevated operating temperatures cause gradual changes to the MOS crystalline structures resulting in long term instability of the sensor devices. Other CO sensors have been constructed from tin oxide, and these have a typical operating temperatures of from 200-250° C. Furthermore, even though the room temperature conductivity of tin oxide can be increased by doping, the doping operation is detrimental in that it decreases the tin oxide's sensitivity to measuring CO. CO sensors with operating temperatures of around 80° C. have been constructed from cobalt oxide. However, it is impractical to use this material as a low-cost room temperature CO sensor because cobalt oxide has an extremely high room temperature resistance. The high room temperature resistance of cobalt oxide necessitates that any CO sensor so constructed would require more sophisticated electronic devices and techniques to monitor the CO sensor's output.

Thus, there is a continuing need for low-cost, easily integratable, CO sensors that operate at ambient temperatures requiring no power source for heating the sensor, to monitor combustion environments to meet government regulations and minimize negative effects of CO on ecosystems and on health.

SUMMARY

A sensor for measuring CO within a gas mixture includes a ruthenium oxide present in a form having one or more surfaces. The gas mixture contacts at least one surface of the ruthenium oxide during operation of the sensor. A pair of conductive electrodes are operatively connected to a surface of the ruthenium oxide contacted by the gas mixture during operation of the sensor. An electrical device is operatively connected to the pair of conductive electrodes. The electrical device is capable of applying a constant potential or, alternatively, a constant current, between the pair of conductive electrodes and measuring a current or, alternatively, a potential, between the pair of conductive electrodes, from which a resistance can be derived as the gas mixture contacts the surface of the ruthenium oxide to which the pair of conductive electrodes are operatively connected.

BRIEF DESCRIPTION OF THE DRAWINGS

In the accompanying drawings which are incorporated in and constitute a part of the specification, embodiments of the invention are illustrated, which, together with a general description of the invention given above, and the detailed description given below, serve to exemplify the embodiments of this invention.

FIGS. 6A and 6B shows graphically the time dependent changes in resistance output in response to changes in CO concentration for an exemplary CO sensor at room temperature.

DETAILED DESCRIPTION

Figure 1:
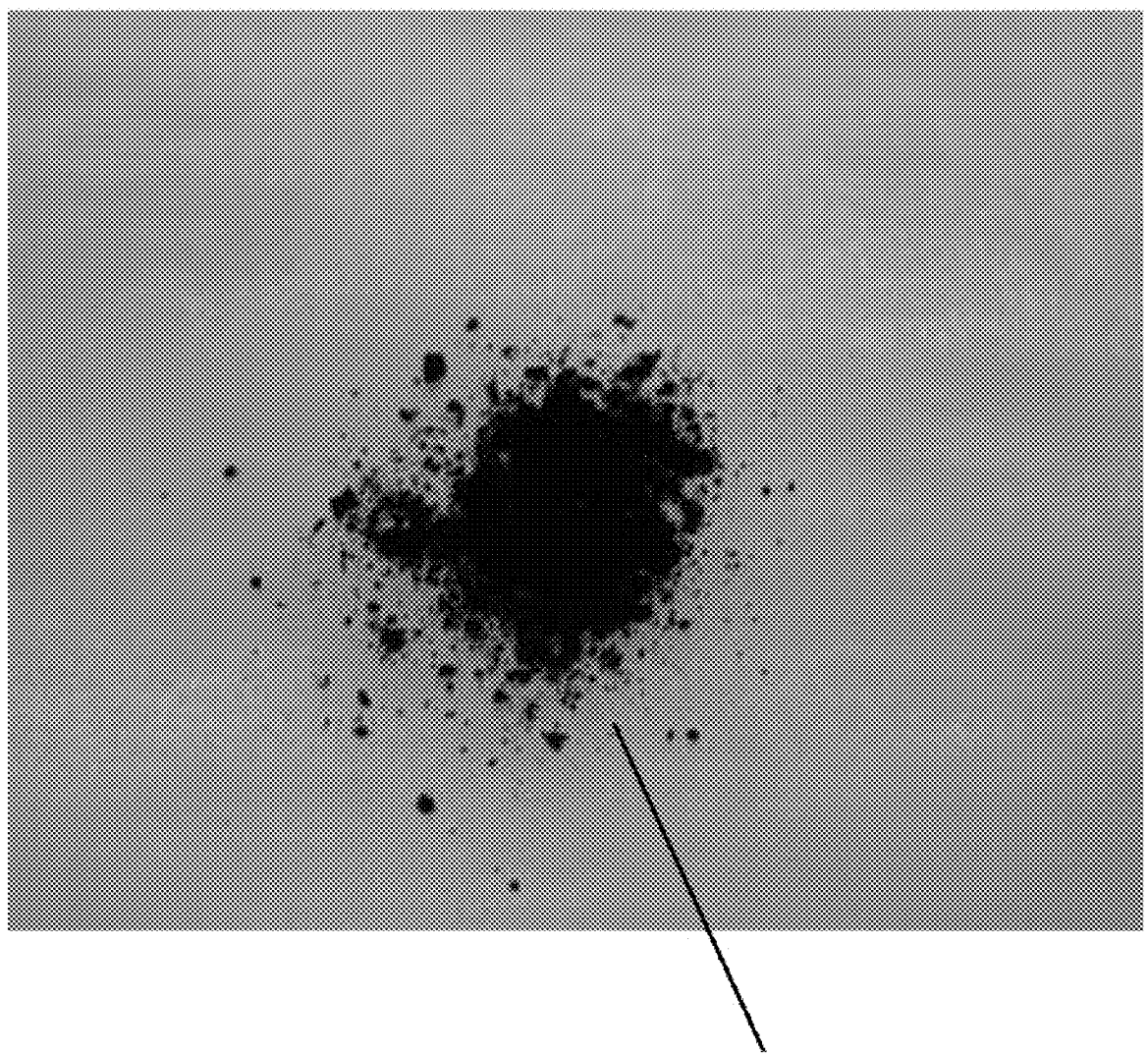
FIG. 1 shows a hydrated ruthenium oxide precipitate that is used in sensor construction.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise. All publications, patent applications, patents, and other references mentioned herein are incorporated by reference in their entirety.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurements.

CO Sensors and Systems

Sensors described herein are for measuring CO concentration in a gas mixture. The resistive-type CO sensor devices of the present invention utilize one or more hydrated metal oxides as the sensing material and rely on CO oxidation as the underlying sensing principle. The invention reduces (or even eliminates) the need for a heating device in a CO sensor, as it operates to sense CO present in gas mixtures at temperature ranges of from about 0° C. to about 300° C., in one embodiment from about 25° C. to about 300° C., or in another embodiment from about 25° C. to about 100° C. For certain embodiments, this includes optimum operation of the CO sensor at ambient temperatures, for example, at room temperature. We contemplate that these sensors may function at CO concentrations of from between 1-10,000 ppm, in one embodiment at CO concentrations of from between 1-1,000 ppm.

Embodiments of the invention include sensors for measuring CO within a gas mixture, wherein the sensor comprises a hydrated metal oxide selected from the group consisting of hydrated iron oxide, hydrated cobalt oxide, hydrated vanadium oxide, hydrated chromium oxide, hydrated ruthenium oxide, and any mixture thereof. The hydrated metal oxide is present in a form having one or more surfaces. The gas mixture contacts at least one surface of the hydrated metal oxide during operation of the sensor. A pair of conductive electrodes are operatively connected to a surface of the hydrated metal oxide, in one embodiment the surface contacting the gas mixture during operation of the sensor, and an electrical device is operatively connected to the pair of conductive electrodes. The electrical device is capable of applying a constant potential or, alternatively, a constant current, between the pair of conductive electrodes and measuring a current or, alternatively, a potential, between the pair of conductive electrodes, from which a resistance can be derived as the gas mixture contacts the surface of the hydrated metal oxide, in one embodiment the surface contacting the gas mixture during sensor operation.

A specific embodiment of the invention includes a sensor for measuring CO within a gas mixture, wherein the sensor comprises a hydrated ruthenium oxide. The hydrated ruthenium oxide is present in a form having one or more surfaces. The gas mixture contacts at least one surface of the hydrated ruthenium oxide during operation of the sensor. A pair of conductive electrodes are operatively connected to a surface of the hydrated ruthenium oxide, in one embodiment the surface contacting the gas mixture during operation of the sensor, and an electrical device is operatively connected to the pair of conductive electrodes. The electrical device is capable of applying a constant potential between the pair of conductive electrodes and measuring a current between the pair of conductive electrodes from which a resistance can be derived, as the gas mixture contacts the surface of the hydrated ruthenium oxide, in one embodiment the surface contacting the gas mixture, during sensor operation.

In certain instances, the sensors herein described operate at a temperature range of from about 0° C. to about 300° C. In other instances the sensors herein described measure CO in the presence of one or more interfering gases. The one or more interfering gases can be selected, for example, from gases such as $CO_2$, $NH_3$, NO, $NO_2$, volatile hydrocarbons, or any combination thereof. Furthermore, the one or more interfering gases may be present, for example, at concentrations of from about 1 ppm to about 1,000 ppm.

In certain embodiments the hydrated metal oxide is in a form of a film, a substrate, a coating, a monolith, or any combination thereof. In other embodiments the hydrated metal oxide is in the form of a coating coated on a support. The pair of conductive electrodes may be, for example, constructed from silver, gold, platinum, palladium, ITO, or any combination thereof. Optionally, the sensors herein described may further comprise a catalyst incorporated into the hydrated metal oxide. Additional embodiments of the invention include a system comprising the CO sensors herein described. The system may, for example, comprise an environmental suit, which includes a space suit. The system may also, for example, comprise a building or a room, or the system may comprise a transportation vehicle, which includes a space vehicle. The system may also be miniaturized to adapt to its environment, for example, sized to fit within or to be part of a cell phone platform or for use within or as part of a fire detector.

Sensor Materials

The nature of the different materials used to construct the claimed CO sensors contribute to many of the CO sensor properties. Types of hydrated metal oxides that are employed and, optionally, the types, amounts, and ratios of varying catalysts that are used in combination with or that are incorporated into the hydrated metal oxides are selected so a resulting sensor will meet performance criteria that is established or that may be desired. The performance criteria are established or may be desired to ensure acceptable and, for certain embodiments, optimal CO sensor performance is achieved at desired and targeted CO concentrations and at desired and targeted temperature ranges.

Hydrated Metal Oxides

The sensors described herein rely on a changing resistivity of a hydrated metal oxide surface, which results due to CO molecules adsorbing and oxidizing on the hydrated metal oxide surface. Suitable hydrated metal oxides for constructing the sensors described may include, for example, hydrated iron oxide, hydrated cobalt oxide, hydrated vanadium oxide, hydrated chromium oxide, hydrated ruthenium oxide, and any mixture thereof. In one embodiment, the hydrated metal oxide precipitate is a hydrated ruthenium oxide. In another embodiment, the hydrated metal oxide precipitate is an amorphous hydrated ruthenium oxide as determined by conventional X-ray powder diffraction methods. In another embodiment, the metal oxide precipitate is a partially crystalline ruthenium oxide as determined by conventional X-ray powder diffraction methods. Other MOS materials, which manifest characteristics and properties similar to hydrated ruthenium oxide or the exemplary materials listed above are also contemplated as suitable for the sensors described. It is important that these metal oxides be good conductors of electricity under ambient temperature conditions.

Without intending to be bound, we believe a mechanism of CO oxidation on the surface of a hydrated metal oxide surface, occurs according to Scheme 1, and is described as follows. The hydrated ruthenium oxide (represented in Scheme 1 as $RuO_xH_y$) may consist primarily of nanocrystals of ruthenium oxide (with ruthenium in the oxidation states of $Ru^{4+}$ and $Ru^{3+}$), water, and a hydroxylated surface. Upon heat treatment, the material may be converted to $RuO_2$ ($Ru^{4+}$) with a substantial loss of $Ru^{3+}$, $H_2O$ and —OH groups. This process may occur at temperatures of about 500° C. or higher. The ruthenium oxide material behaves and has properties of a metallic conductor, with conductivity arising primarily due to the motion of orbital electrons.

In the presence of CO, it is contemplated that the conduction mechanisms involving the electron hopping and the lower valent ruthenium are being influenced. Electron conduction occurs by hopping of electrons between 20-50 nm particles in a percolative fashion. Thus, any interference to this hopping process will decrease conductivity. In the presence of CO, carbonates are adsorbed to the $RuO_x(OH)_y$ surface. The carbonates formed on the surface of $RuO_x(OH)_y$ will impede the electron hopping between the $RuO_2$ crystallites in the $RuO_x(OH)_y$ network, resulting in the decrease of conductivity in the presence of CO. In addition, the CO can also reduce the Ru(IV) to lower valent ruthenium (e.g. Ru(III)), which should also lower the conductivity. Upon introduction of $O_2$, both these processes can be reversed and the conductivity is restored. This mechanism is fundamentally different from all semiconducting based oxide sensors, since in such materials the intrinsic conductivity of the oxide is changed in the presence of gas due to modifications in chemisorbed oxygen. This is manifested in the conductivity of the conventional semiconducting oxides such as $SnO_2$ where the resistance of a thick film (hundreds of microns) is in the kiloOhm to megaOhm range even at elevated temperatures, whereas the resistance of a comparable metal like ruthenium oxide film is of the order of Ohms even at room temperature.

Scheme 1

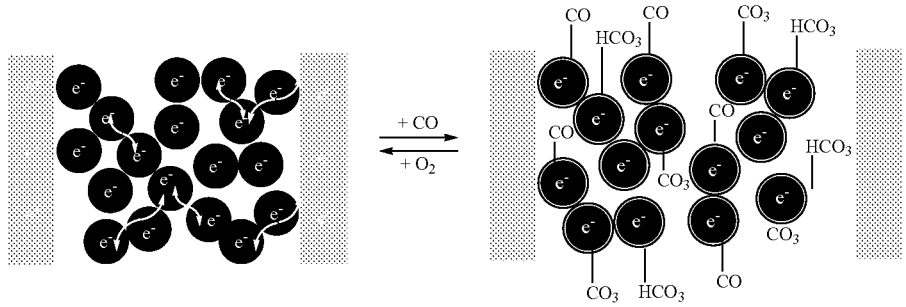

In certain embodiments, in order to perform optimally as a CO sensor material, a $RuO_xH_y$ may have the appropriate balance of $Ru^{3+}$ and $Ru^{4+}$. Consequently, it is contemplated that at too high of levels of $Ru^{4+}$ the measured conductivity of $RuO_xH_y$ may be overwhelming and CO oxidation would lead to minimal change in the materials resistance. OH groups may facilitate low temperature CO oxidation, since they are relevant in the formation of intermediate bicarbonate species. Thus it is also contemplated that extensive drying of the sample under vacuum, which is a way to keep the $Ru^{3+}/Ru^{4+}$ ratio of the material constant, may decrease CO oxidation. Conversely, it is contemplated that if the $Ru^{3+}$ level is too high the material will be a poor conductor. Consequently, at higher temperatures the sensor performance of certain embodiments may degrade due both to loss of —OH groups and $Ru^{3+}$ to $Ru^{4+}$ conversion and growth of crystal size. It is also contemplated that higher surface area $RuO_xH_y$ materials will show an increase in CO sensitivity. It is additionally contemplated that other materials suitable for exhibiting room temperature CO sensing in this regard include, for example, hydrated $Fe_2O_3$, $CO_2O_4$, $V_2O_5$, $Cr_2O_3$.

Catalysts

An optional ingredient that may be incorporated into the hydrated metal oxide is a catalyst. It is contemplated that the incorporation of catalysts into the hydrated metal oxides will provide the sensors with additional desirable attributes. For example, some catalysts, such as Au, are useful for promoting CO oxidation and they are therefore contemplated as being useful for increasing the sensors response. Certain catalysts are also useful for promoting carbonate decomposition. Therefore, such catalysts are contemplated as useful for promoting carbonate/bicarbonate formation, which may influence the sensor response and recovery times. The properties of selected catalysts, in combination with the natural properties of the selected hydrated metal oxide materials, can be used together to ensure that sensors constructed from the hydrated metal oxides are operational over a wide range of temperatures and CO concentrations, and have tunable selectivity to CO, and have high tolerance for interfering gases that may be present.

Any catalyst that promotes CO oxidation or that promotes carbonate/bicarbonate formation is suitable for use. Suitable catalysts include, for example, Au, Pt, Pd, Rh, Ru, and any combination thereof. The catalyst can be incorporated into the hydrated metal oxides at any point during synthesis. In certain situations, one or more catalysts can be incorporated by impregnation after the hydrated metal oxide sensing material has been precipitated. In other situations, one or more catalysts can be introduced and incorporated into the hydrated metal oxide sensing material by co-precipitation. In certain embodiments, a catalyst having such characteristics is incorporated into the hydrated ruthenium oxide sensor material at from about 100 ppm to about 2,000 ppm. Tables 1a and 1b provide a lists of metal oxides and catalysts that are suitable for use in constructing the CO sensors described herein. Any of the catalysts listed in Table 1b can be used with any of the metal oxides listed in Table 1a.

TABLE 1a

Metal oxides for CO sensors
Metal Oxides $Fe(OH)_x$
Ti doped $\alpha\text{-}Fe_2O_3$
FeO
$\alpha\text{-}Fe_2O_3$
$Co_2SnO_4$
$Co_3O_4 + SnO_2$
$ZnO/SiO_2$
ZnO
$Co_3O_4$
$TiO_2$
NiO
$SnO_2$ TABLE 1b Catalysts for CO sensors
Catalysts Au
Pt
Pd
Rh
Ru
Au—$Mg(OH)_2$ or Au—MgO
Au—$ZrO_2$
Hydrous PdO
CuO
$Cu_2O$
Au—$CeO_2$
Au—$Al_2O_3$ Other additives or compounds may be present in the hydrated metal oxide, in limited or trace amounts, provided that such additives or compounds do not materially change the final properties of the sensors.

As previously indicated, the hydrated metal oxide precipitates can be molded or cast into a variety of shapes and forms including being cast in the form of a film or coating, including a film or coating on another supporting substrate, or it can be cast or shaped into a self-supporting substrate or a monolith. Suitable forms of the hydrated metal oxide have one or more surfaces which can be exposed to the gas mixture during sensor operation. For example, in certain exemplary embodiments, the hydrated metal oxide precipitate is an amorphous hydrated ruthenium oxide in the form of a film or coating, applied to a pair of inter-digitated conducting electrodes which are themselves supported on an alumina substrate.

Conductive Electrodes

The pair of conductive electrodes can be constructed from, for example, gold, platinum, silver, any room temperature conducting metallic material, any room temperature electronic conducting metal oxide materials, any conducting room temperature polymer, or any combination thereof. In order for the sensor to function, the pair of electrodes are operatively connected to the surface of the hydrated metal oxide, in one embodiment the surface contacting the gas mixture during operation of the sensor, and are operatively connected to the electrical device that is used to measure the resistance in response to CO concentration. In this way, the electrodes put the hydrated metal oxide into electrical communication with the electrical device that is used to measure the hydrated metal oxide's electrical resistance. In certain embodiments, the pair of conductive electrodes will be inter-digitated and disposed onto a surface of the hydrated metal oxide, in one embodiment the surface contacting the gas mixture during operation of the sensor.

Electrical Device

Any commercial or noncommercial electrical device capable of measuring electrical resistance can be used in sensor construction. For example, in certain embodiments suitable commercial devices will be used to apply a potential, in one embodiment a constant potential, between the pair of inter-digitated conductive electrodes and measure the current generated between the pair of inter-digitated conductive electrodes. Alternatively, in certain other embodiments, suitable commercial devices will be used to apply a current, in one embodiment a constant current, between the pair of inter-digitated conductive electrodes and measure the voltage generated between the pair of inter-digitated conductive electrodes. In certain exemplary embodiments the electrical device is simply an ohmmeter. In other embodiments the electrical device will be incorporated, along with the entire sensor, as part of an electric circuit board. Still further, such an electric circuit board may be incorporated into a computer.

Methods

Methods for Making Sensors

Embodiments of the invention also include a method for making a CO sensor. In one instance, the method comprises the steps of operatively connecting a coating, substrate, or film of hydrate metal oxide to a pair of conductive electrodes, and operatively connecting an electrical device to this pair of conductive electrodes. The hydrated metal oxide used in such embodiments is selected from the group consisting of hydrated iron oxide, hydrated cobalt oxide, hydrated vanadium oxide, hydrated chromium oxide, hydrated ruthenium oxide, and any mixture thereof. The hydrate metal oxide powder can be deposited and thereby operatively connected to the pair of electrodes by any suitable technique which are known, including, for example, techniques such as impregnation, drop-coating, spin-coating, immersion, and any combination thereof. The electrical device is capable of applying a constant potential, or alternatively a constant current, between the pair of conductive electrodes and measuring a current, or alternatively a potential, between the pair of conductive electrodes. A resistance can then be derived from this measurement, as a gas mixture contacts one or more surfaces of the coating, substrate, or film of hydrated metal oxide.

Certain embodiments of the invention include a method for making a CO sensor, wherein the method comprises combining $RuCl_3$ and NaOH to form a hydrated ruthenium oxide; dispersing this hydrated ruthenium oxide in water; spin coating the dispersion of hydrated ruthenium oxide onto a pair of inter-digitized conductive electrodes; removing the water to form a coating, substrate, or film of the hydrated ruthenium oxide operatively connected to the pair of inter-digitized conductive electrodes; and operatively connecting an electrical device to the pair of inter-digitized conductive electrodes. Again, the electrical device is capable of applying a potential (or alternatively a current) between the pair of inter-digitized conductive electrodes and measuring a current (or alternatively a potential) between the pair of inter-digitized conductive electrodes and a resistance can be derived as a gas mixture contacts one or more surfaces of the hydrated ruthenium oxide.

The methods are used to produce sensors that operate at a temperature range of from about 0° C. to about 300° C., in one embodiment the sensors operate at a temperature range of from about 0° C. to about 100° C., in another embodiment the sensor operate at a temperature range of from about 25° C. to about 100° C. Alternatively, the sensors operate at a temperature range of from about 25° C. to about 300° C. In still other embodiments, the methods are used to produce sensors capable of detecting CO in a gas mixture when the concentration of CO contained within the gas mixture is present at concentrations of from about 1 ppm to about 10,000 ppm, in one embodiment the concentration of CO contained within a gas mixture is present at concentrations of from about 1 ppm to about 1,000 ppm.

Response and Recovery Times

A sensor's response time is defined as the amount of time required for the sensor to exhibit 90% of the total response the sensor will exhibit in response to exposure to a source of CO concentration. A sensor's recovery time is similarly defined as the amount of time required for the sensor to exhibit 90% of a recovery back to baseline upon removal from exposure to a source of CO concentration. The sensors produced according to the methods herein described have response and recovery times on the order of minutes.

An exemplary device may be fabricated from hydrated ruthenium oxide, which is produced as a precipitate from the reaction of ruthenium chloride ($RuCl_xH_2O$) with sodium hydroxide (NaOH). In certain exemplary embodiments the hydrated ruthenium oxide used to construct the sensors may also be amorphous. In some instances, the reaction is carried out in an aqueous medium. The resulting precipitate material obtained is washed with deionized water several times, and then dried to remove the excess water. In some instances the precipitate is dried further, prior to use in sensor construction. The resultant powder is redispersed in water and spin coated onto a clean pair of gold inter-digitated electrodes. The coating of hydrated ruthenium oxide is then again dried to remove excess water and this ensures proper contact with the surface of the electrodes is obtained. The pair of gold electrodes are connected to an electrical device, which measures the changes in resistance of the hydrated ruthenium oxide due to the presence of CO, and this change is correlated to a measured CO concentration. The device can be used to detect and measure CO at 25° C., at varying concentrations, for example from about 1-10,000 ppm, in a controlled temperature environment.

Methods of Measuring CO

Embodiments of the invention also include methods for measuring concentration of CO contained in a gas mixture. The method comprises the steps of exposing the sensors described herein to the gas mixture; measuring the current or potential between the pair of conductive electrodes, from which a resistance can be derived, while the sensor is exposed to the gas mixture; and calibrating the measured current or potential to the concentration of CO contained in the gas mixture. In certain examples, the sensor used in the methods comprises a hydrated ruthenium oxide present in a form having one or more surfaces, wherein the gas mixture contacts at least one surface of the hydrated ruthenium oxide during operation of the sensor; a pair of conductive electrodes operatively connected to a surface of the hydrated ruthenium oxide, in one embodiment the surface contacting the gas mixture during operation of the sensor; and an electrical device operatively connected to the pair of conductive electrodes, wherein the electrical device is capable of applying a potential or, alternatively, a current, between the pair of conductive electrodes and measuring a current or, alternatively, a potential, between the pair of conductive electrodes, from which a resistance can be derived as the gas mixture contacts the at least one surface of the hydrated ruthenium oxide.

Additional embodiments of the invention include a method for measuring concentration of CO contained in a gas mixture, comprising the steps of exposing a sensor to the gas mixture; measuring the current or potential between the pair of conductive electrodes while the sensor is exposed to the gas mixture; and calibrating the measured current or potential or the resistance derived from it to the concentration of CO contained in the gas mixture. In certain examples, the sensor used comprises a hydrated metal oxide selected from the group consisting of hydrated iron oxide, hydrated cobalt oxide, hydrated vanadium oxide, hydrated chromium oxide, hydrated ruthenium oxide, and any mixture thereof, wherein the amorphous metal oxide is present in a form having one or more surfaces, and wherein the gas mixture contacts at least one surface of the amorphous metal oxide during operation of the sensor; a pair of conductive electrodes operatively connected to a surface of the hydrated metal oxide, in one embodiment the surface contacting the gas mixture during operation of the sensor; and an electrical device operatively connected to the pair of conductive electrodes, wherein the electrical device is capable of applying a potential or a current between the pair of conductive electrodes and measuring a current or a potential between the pair of conductive electrodes as the gas mixture contacts the at least one surface of the hydrated metal oxide.

Operating Temperatures and CO Concentrations

The sensors described herein can be used with the methods described herein to measure the concentration of CO in a gas mixture at temperatures ranging from about 0° C. to about 300° C., in one embodiment at temperatures ranging from about 0° C. to about 100° C., in another embodiment at temperatures ranging from about 25° C. to about 100° C., in another embodiment at temperatures ranging from about 25° C. to about 100° C. Alternatively, the sensors described herein can be used with the methods described herein to measure the concentration of CO in a gas mixture at temperatures ranging from about 25° C. to about 300° C. The sensors described herein can be used with the methods described herein to measure the concentration of CO in a gas mixture when the concentration of CO contained within the gas mixture is present at concentrations of from about 1 ppm to about 10,000 ppm, in one embodiment when the concentration of CO contained within a gas mixture is present at concentrations of from about 1 ppm to about 1,000 ppm.

EXAMPLES

The present invention will be understood by those skilled in the art by reference to the CO sensors and an evaluation of these CO sensors performance provided in the accompanying figures. While various embodiments of the present invention are described with reference to the figures and the data presented therein, this data only illustrates different embodiments and should not limit the scope of the present invention.

Example 1

Construction

A sensor device was fabricated from hydrated ruthenium oxide ($RuO_xH_y$). The hydrated ruthenium oxide was a product of a precipitation reaction of ruthenium chloride ($RuCl_3.XH_2O$) with sodium hydroxide (NaOH). The amorphous hydrated ruthenium oxide sensing material contained 500 ppm of Au as a catalyst. The catalyst was incorporated using standard impregnation techniques. The synthesized material was then spin coated onto a pair of inter-digitated gold electrodes (10 mm×15 mm).

Some exemplary synthetic methods for making the sensors herein described are summarized in the flow charts shown below (Schemes 2(a)-(c)). Scheme 2(a) shows a generic representation of a fabrication method used to produce a hydrated ruthenium oxide sensing material. The hydrated ruthenium oxide is produced as a precipitation in a reaction between ruthenium chloride ($RuCl_3.XH_2O$) and sodium hydroxide (NaOH). Scheme 2(b) and 2(c) show generic representations of a fabrication method used to produce a hydrated ruthenium oxide sensing material having a catalyst material incorporated within the material. Scheme 2(b) shows an impregnation technique that involves introducing the catalyst into the amorphous metal oxide sensing material after the sensing material has been precipitated. Scheme 2(c) shows a co-precipitation technique that involves simultaneously precipitating the catalyst and the amorphous metal oxide sensing material together in order to incorporate the catalyst into the amorphous metal oxide sensing material.

SCHEME 2

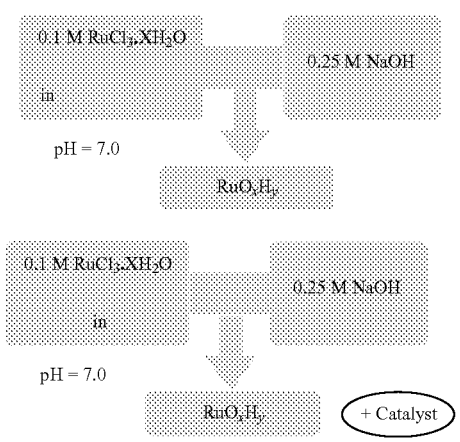

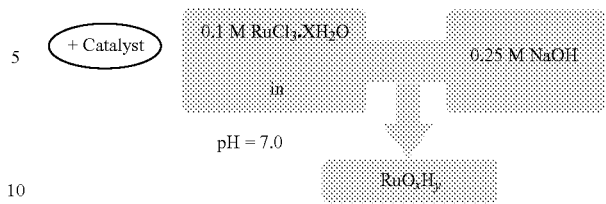

Referring now to the figures, FIG. 1 shows the amorphous powder that results 10 from the precipitation reaction between ruthenium chloride ($RuCl_3.XH_2O$) and sodium hydroxide (NaOH) after the precipitate was dried and excess water was removed. This precipitate was redispersed into water and this dispersion was deposited onto a pair of clean, gold inter-digitated electrodes.

Figure 2A:
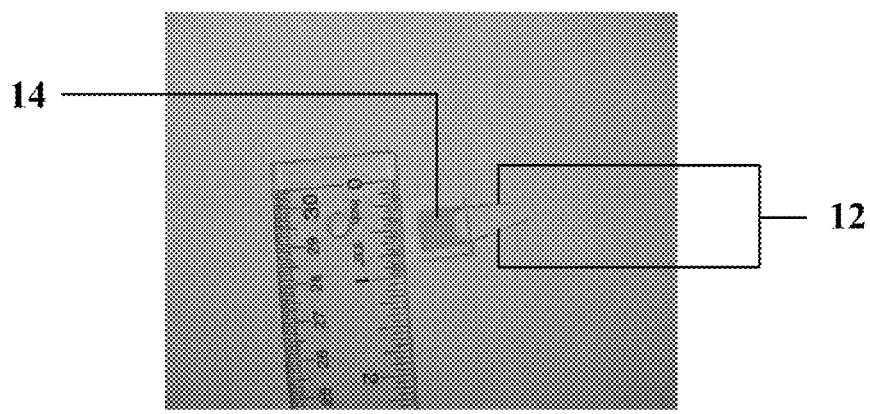
FIGS. 2A, 2B, and 2C show the stepwise deposition of a hydrated ruthenium oxide onto a pair of inter-digitated gold electrodes supported on alumina.
Figure 2B:
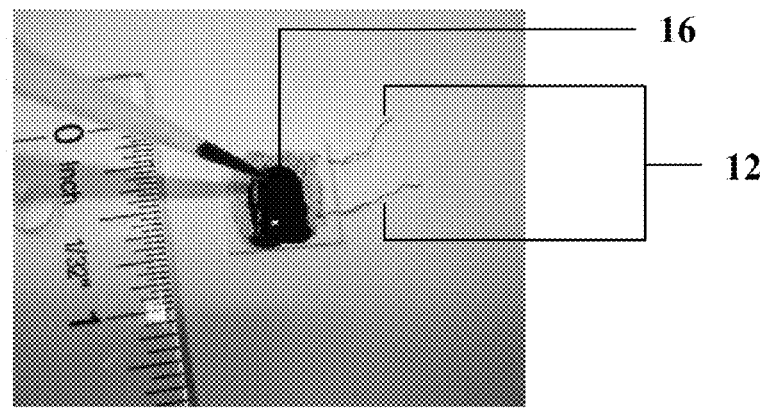
Figure 2C:
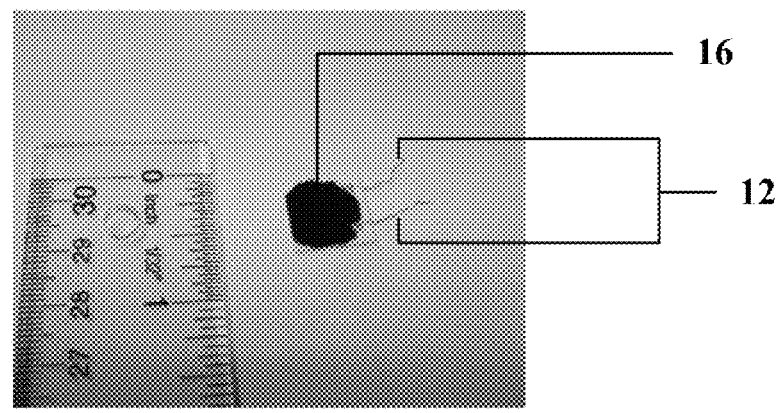

FIG. 2A shows the stepwise preparation of the exemplary sensor device of Example 1. FIG. 2(a) shows a pair of inter-digitated electrodes 12 supported on an aluminum oxide substrate 14 before the amorphous hydrated ruthenium oxide sensing material is deposited. FIGS. 2B and 2C show consecutively the progressive deposition of amorphous hydrated ruthenium oxide 16 onto the pair of inter-digitated gold electrodes 12, which demonstrates construction of sensor device of Example 1.

Figure 3:
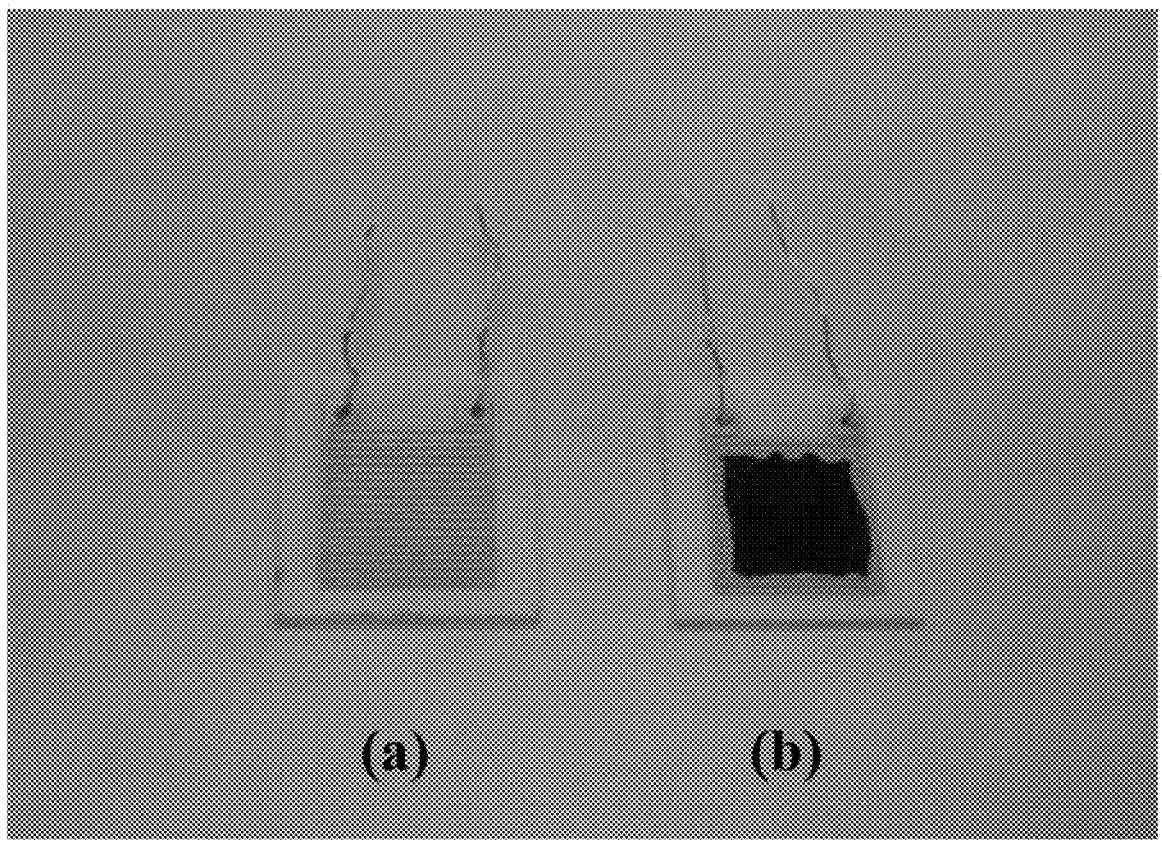
FIG. 3 shows a pair of inter-digitated gold electrodes before and after hydrated ruthenium oxide is deposited thereon.

FIG. 3 shows the pair of inter-digitated electrodes before (a) and after (b) deposition of the sensing material is completed. The finished device, which is show in (b), was dried at a temperature of about 25° C. to remove water and ensure proper contact of the amorphous hydrated ruthenium oxide with the electrode surface is achieved.

Performance

Figure 4:
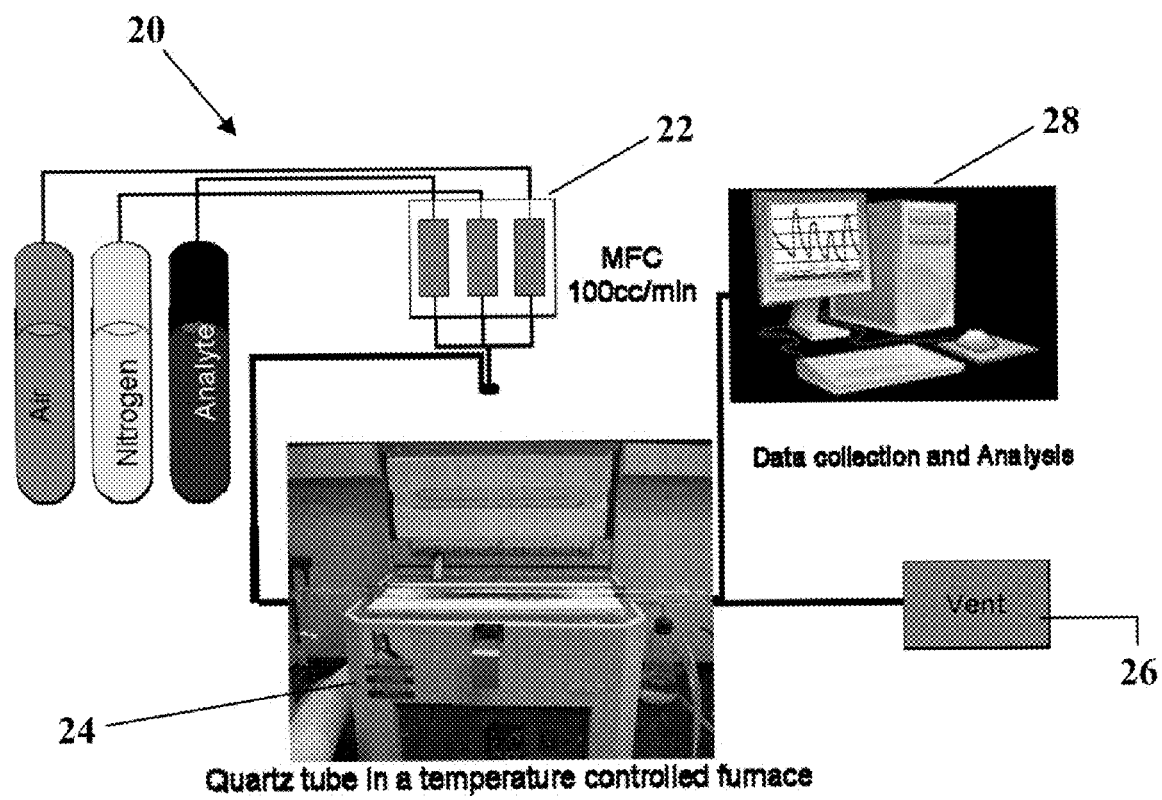
FIG. 4 shows an example sensor testing apparatus.

To test the sensor of Example 1, a series of experiments were conducted having the set-up shown in FIG. 4. An example sensor device 20 was tested within a quartz tube at 25° C. in a temperature controlled oven, as shown in FIG. 4. Mass flow controllers 22 (e.g., quartz tubes in a temperature controlled furnace 24) were used to vary the concentrations of CO present (from 32-1000 ppm) in a gas mixture. The CO is safely disposed through a vent 26. The gas mixture contained varying concentrations of CO within a synthetically prepared air. The synthetically prepared air has a composition that mimics the composition of natural air and is comprised of about 21% oxygen with the balance being nitrogen. The CO containing gas mixtures were passed over the sensor device at varying rates (from 100-500 cc/min). The change in resistance exhibited by the exemplary sensor device was measured using a multimeter. The multimeter applied a current of 1 milliamp between the two inter-digitated electrodes, subsequently recorded the potential and then derived a resistance as a function of time as the CO containing gas mixture was in contact with a surface of the sensor device. The data is collected and analyzed by a computing device 28.

The data shown in the figures indicates that the CO sensors described and exemplified herein are very useful. For instance, the sensor of Example 1 was able to detect from about 32 to about 1,000 ppm CO in a synthetic air background at room temperature. The response of the sensor of Example 1 was also highly reproducible, and this response indicated that the sensor exhibits selectivity to CO over other gases. Attributes associated with optimal performance of the sensor of Example 1 include: (i) having a detection range of 1-1,000 ppm CO; (ii) having an optimal operation at temperatures of from 25° C.-300° C.; (iii) exhibiting minimal interferences from humidity; (iv) exhibiting no sensitivity to ambient concentrations of carbon dioxide, methane, propane, ammonia, NO and $NO_2$; and (v) an improved stability when a catalyst is incorporated into the amorphous hydrated ruthenium oxide sensing material.

Figure 5:
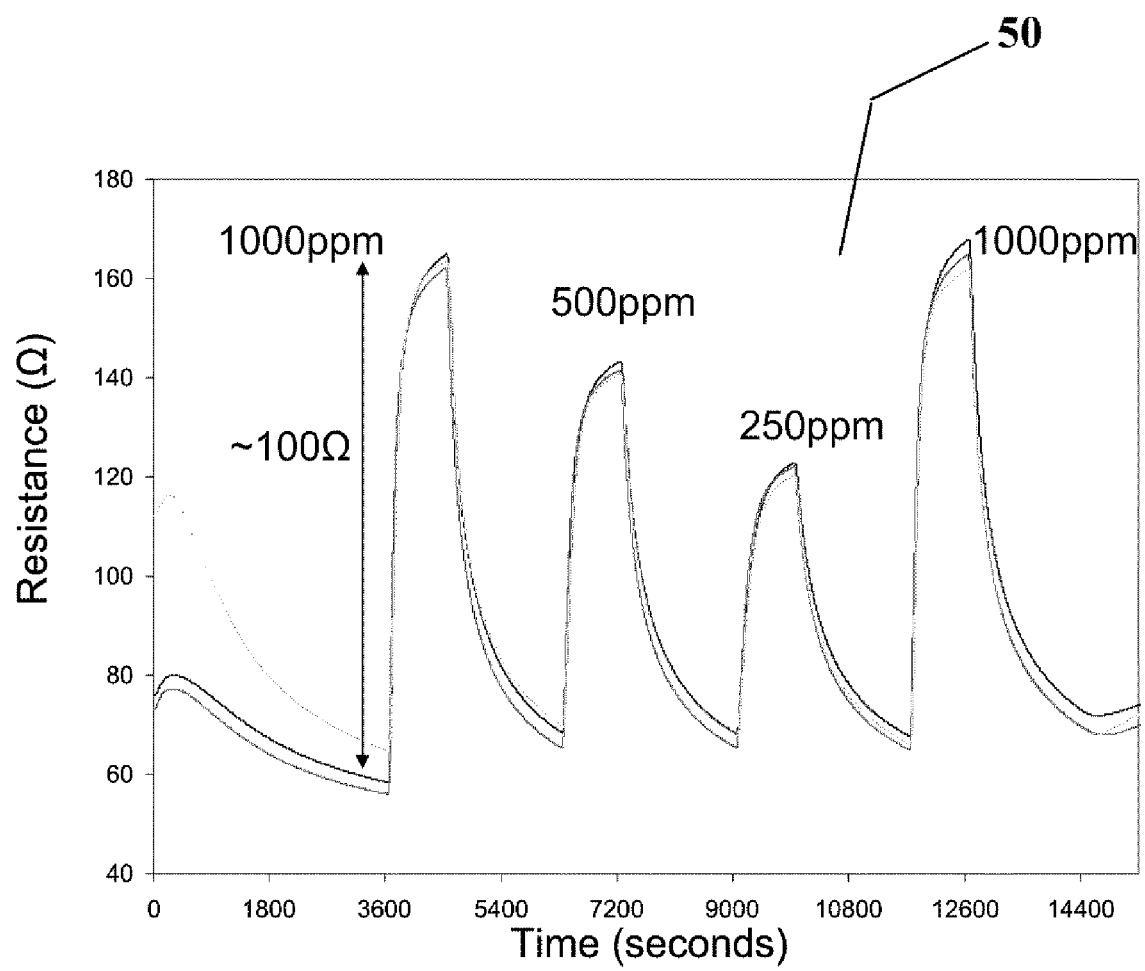
FIG. 5 shows response curves for three separate CO sensors demonstrating the reproducibility of both sensor construction and performance at room temperature.

FIG. 5, which illustrates a graph 50 of resistance vs. time, shows that the sensor device of Example 1 has the capacity to measure CO in air at 25° C. and that this capacity is highly reproducible, over a range of CO concentrations from 100-1000 ppm. The sensor device of Example 1 was exposed to alternating concentrations of CO and the sensor's response and recovery was graphed. The sensor device of Example 1 was exposed to CO concentrations in synthetic air, which cycled between 0-1000 ppm, 0-500 ppm, 0-250 ppm, and 0-100 ppm. This cyclical exposure was repeated with three separately prepared sensors. As FIG. 5 shows, separate sensor devices prepared according to Example 1 performed very consistently at 25° C., which indicates that both the preparation and the performance of the sensors described herein is very reproducible.

FIGS. 6A and 6B demonstrate that the sensor device of Example 1 has response and recovery times on the order of minutes, and that this response is reliable over CO concentrations ranging from 32-250 ppm. FIG. 6A illustrates a graph 52 of resistance vs. time that shows the response of the sensor device of Example 1 to repeated exposure of varying CO concentrations, which cycle between 0-250 ppm, in air at about 25° C. FIG. 6B illustrates a graph 54 of resistance vs. time that shows the response of the sensor device of Example 1 to repeated exposure of varying CO concentrations, which cycle between 0-32 ppm, in air at about 25° C. As FIGS. 6A and 6B show, the sensor device of Example 1 has response times and recovery times that are on the order of minutes at 25° C., and at CO concentrations ranging from 0-250 ppm.

Figure 7:
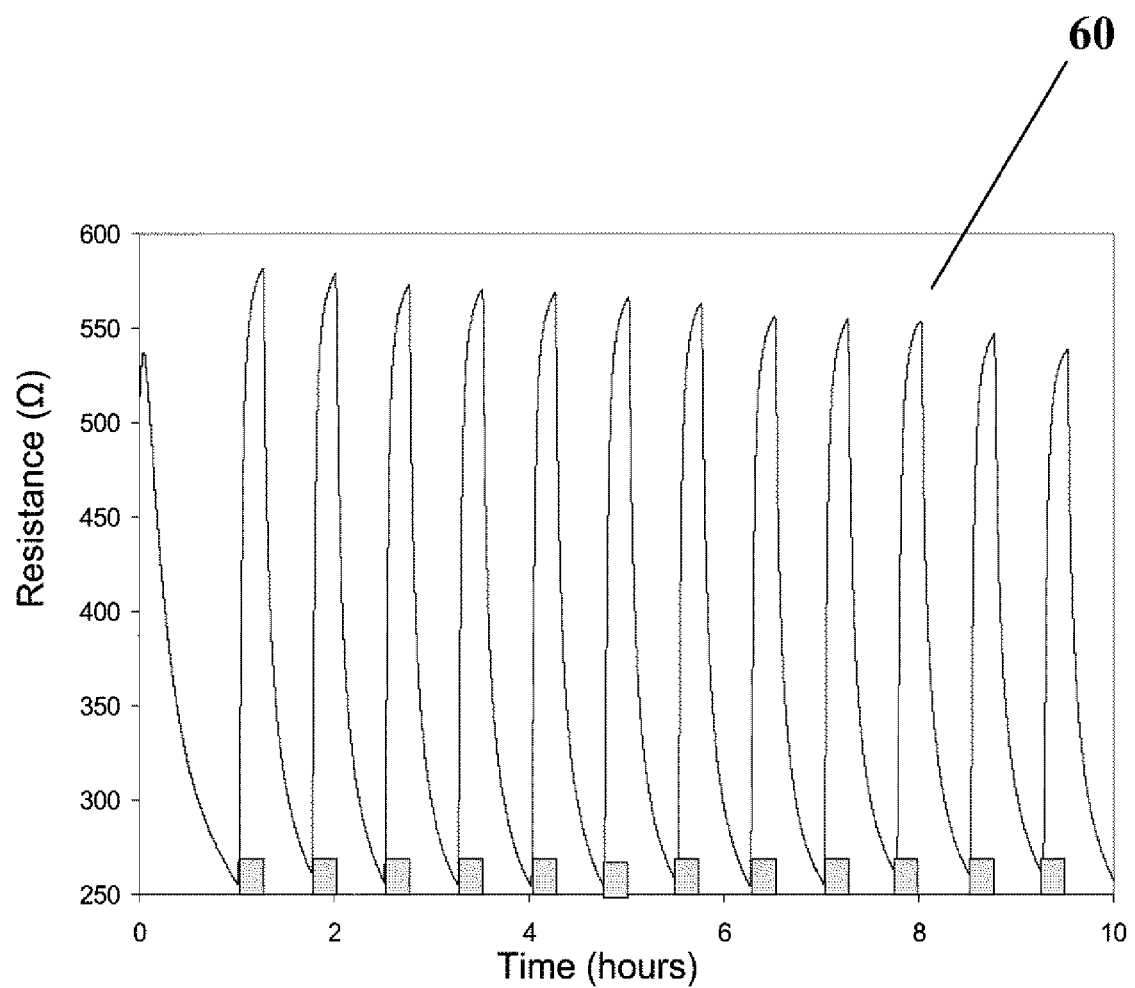
FIG. 7 shows graphically the time dependent changes in resistance output in response to changes in CO concentration for an exemplary CO sensor modified with Au catalyst at room temperature.

FIG. 7 illustrates a graph 60 of resistance vs. time that demonstrates that the long term stability of the sensor device of Example 1 can be enhanced by the addition of an Au catalyst to the amorphous hydrated ruthenium oxide sensing material. As FIG. 7 shows, the sensor's long term response to changes in CO concentration, when exposed to varying CO concentrations which cycle between 0-250 ppm CO in air at about 25° C., remains stable for over 10 hours.

COMPARATIVE EXAMPLES

Several comparative examples of known CO sensors, along with the details of their principle of operation and their corresponding properties and limitations are provided in Table 2. As described and exemplified above, the claimed CO sensors of the present invention have demonstrable benefits over other resistive-type CO sensors that are listed in Table 2. Further benefits associated with the CO sensors of the present invention stem from (i) the lowered manufacturing costs associated with producing the hydrated MOS sensor material; (ii) the sensors herein described can be combined with and integrally connected to simple electronics; and (iii) the sensors herein described have desirable response features, including high CO sensitivity desirable response and recoverability upon exposure to gases mixtures containing CO.

TABLE 2

| Known Room Temperature CO Sensors and Properties | | | |
|---|---|---|---|
| Material | Sensing Principle | Response/ Recovery Times | Limitations |
| AMPEROMETRIC DEVICES | | | |
| Nafion- electrochemical cell | fuel cell principle | minutes | Requires an $H_2O$ reservoir |
| $Sb_2O_5 \cdot 2H_2O$ | proton conductor | minutes | CO and $H_2$ produce similar signals Detection limit of 1000 ppm |
| CAPACITIVE DEVICES | | | |
| Nafion-Pt cloth | changing capacitance, kinetics of charge transfer | n/a | n/a |
| Nafion-Pt/Pt—Ru | fuel cell principle | minutes | Impractical for current applications |
| Material | Sensing Principle | Response/ Recovery Times | Features/Limitations |
| SHOTTKY-FET-TRANSISTOR DEVICES | | | |
| Au/GaAs | changing Schottky barrier | seconds | Only tested with $N_2$ background |
| ITO/GaAs | changing Schottky barrier | seconds | Only tested with $N_2$ background |
| CNT-FET | heme-Fe:CO interaction | seconds | Only tested with $N_2$ background |
| SWNT- transistors | SWNT-COOH:CO interaction | minutes | Problems in air |
| SAW DEVICES | | | |
| Polyaniline- $In_2O_3$ | conductivity change coupled with SAW device | seconds | Long term stability |
| I-V COUPLED DEVICES | | | |
| Porous Silicon | n/a | minutes | Not practical at ambient conditions |
| CNT on $Co_3O_4$—$SnO_2$ | adsorption/desorption | seconds | 20 ppm limit Selectivity is questionable |
| $Co_3O_4$ | CO oxidation | seconds | 4 ppm $CH_4$ response is the same as 4 ppm CO |
| $SnO_2$/CNT | CO oxidation | n/a | 47 ppm limit Steady state only No transient data available |
| Pt—$SnO_2$ | CO oxidation | minutes | 5000 ppm limit |

TABLE 2-continued

Known Room Temperature CO Sensors and Properties

| | | | |
|---|---|---|---|
| Au—$SnO_2$ on CNT | n/a | minutes | Sensitivity not practical 500 ppm limit Not practical at ambient conditions |

RESISTIVE DEVICES

| | | | |
|---|---|---|---|
| Polyaniline-$TiO_2$ | polyaniline senses CO | minutes | Interferences an issue |
| Polyaniline zeolite | Polyaniline senses CO | minutes | n/a |
| Polypyrrole-ferrocene | Pyrrole:CO interaction | minutes | Moisture a problem |
| Pt—$SnO_2$ | CO oxidation | minutes | 300 ppm limit |
| Au—$Fe_2O_3$ | CO oxidation | minutes | 50% RH 200 ppm limit at 200° C. No data for RT. |
| Mn—$Fe_3O_4$ | n/a | seconds | Sensor response comparable with $H_2O$, EtOH, $NO_2$ and $H_2$ Baseline established in vacuum Requires 20mTorr at RT. |
| Au/$Co_3O_4$ | CO oxidation | minutes | High background resistance requires electronic correction 80° C. operating temperature. |

While the present invention has been illustrated by the description of embodiments thereof and while the embodiments have been described in some detail, it is not the intention of the applicant to restrict or in any way limit the scope of the appended claims to such detail. Additional advantages and modifications will readily appear to those skilled in the art. Therefore, the invention in its broader aspects is not limited to the specific details, representative apparatus and methods, and illustrative examples shown and described. Accordingly, departures may be made from such details without departing from the spirit or scope of the applicant's general inventive concept.

What is claimed is:

1. A sensor for measuring CO within a gas mixture, wherein the sensor comprises:
   a. a ruthenium oxide present in a form having one or more surfaces, wherein the gas mixture contacts at least one surface of the ruthenium oxide during operation of the sensor;
   b. a pair of conductive electrodes operatively connected to a surface of the ruthenium oxide contacted by the gas mixture during operation of the sensor; and
   c. an electrical device operatively connected to the pair of conductive electrodes, wherein the electrical device is capable of applying a constant potential or, alternatively, a constant current, between the pair of conductive electrodes and measuring a current or, alternatively, a potential, between the pair of conductive electrodes, from which a resistance can be derived as the gas mixture contacts the surface of the ruthenium oxide to which the pair of conductive electrodes are operatively connected.

2. The sensor of claim 1 wherein the ruthenium oxide is at least partially hydrated.

3. The sensor of claim 1 wherein the ruthenium oxide is one of i) amorphous by conventional powder X-ray diffraction methods and ii) partially crystalline by conventional powder X-ray diffraction methods.

4. The sensor of claim 1 further comprising a catalyst incorporated into the ruthenium oxide.

5. The sensor of claim 1 having a response time to 90% of steady state signal of ten minutes.

6. The sensor of claim 1 having a recovery time to 90% of steady state signal of ten minutes.

7. The sensor of claim 1 wherein the ruthenium oxide is precipitated from an aqueous reaction between $RuCl_3$ and NaOH.

8. The sensor of claim 7 wherein the ruthenium oxide precipitated from an aqueous reaction between $RuCl_3$ and NaOH is dried prior to use in the sensor.

9. The sensor of claim 8 wherein the ruthenium oxide is in the form of a coating coated on a support.

10. The sensor of claim 1 wherein the ruthenium oxide is in a form of a film, a substrate, a coating, a monolith, or any combination thereof.

11. A system comprising the sensor of claim 1.

12. The system of claim 11, further comprising an environmental suit, the sensor being used in the environmental suit.

13. The system of claim 11, further comprising a building or a room, the sensor being used in the building or room.

14. The system of claim 11, further comprising a transportation vehicle, the sensor being used in the transportation vehicle.

15. The system of claim 11, further comprising a cell phone platform, the sensor being used with the cell phone platform.

16. A sensor for measuring CO within a gas mixture, wherein the sensor comprises:
   a. a metal oxide selected from the group consisting of iron oxide, cobalt oxide, vanadium oxide, chromium oxide, ruthenium oxide, and any mixture thereof, wherein the metal oxide is present in a form having one or more surfaces, and wherein the gas mixture contacts at least one surface of the metal oxide during operation of the sensor;
   b. a pair of conductive electrodes operatively connected to a surface of the hydrated metal oxide; and
   c. an electrical device operatively connected to the pair of conductive electrodes, wherein the electrical device is capable of applying a constant potential or, alternatively, a constant current, between the pair of conductive electrodes and measuring a current or, alternatively, a potential, between the pair of conductive electrodes, from which a resistance can be derived as the gas mixture contacts the surface of the hydrated metal oxide to which the pair of conductive electrodes are operatively connected.

17. The sensor of claim 16 wherein the metal oxides are at least partially hydrated.

18. The sensor of claim 16 further comprising a catalyst incorporated into the ruthenium oxide.

19. The sensor of claim 16 wherein the sensor operates at a temperature range of from about 0° C. to about 300° C.

20. The sensor of claim 16 wherein the sensor measures CO within a gas mixture when CO is present at concentrations of from about 1 ppm to about 1,000 ppm.

21. The sensor of claim 16 wherein the sensor measures CO in the presence of one or more interfering gases.

22. The sensor of claim 21 wherein the one or more interfering gases are selected from the group consisting of $CO_2$, $NH_3$, $NO$, $NO_2$, volatile hydrocarbons, and any combination thereof.

23. The sensor of claim 22 wherein the one or more interfering gases are present at concentrations of from about 1 ppm to about 1,000 ppm.

24. The sensor of claim 16 wherein the pair of conductive electrodes is constructed from silver, gold, platinum, palladium, ITO, or any combination thereof.

25. A method for measuring concentration of CO contained in a gas mixture, wherein the method comprises the steps of:
   a. exposing a sensor to the gas mixture,
      wherein the sensor comprises:
         a metal oxide selected from the group consisting of iron oxide, cobalt oxide, vanadium oxide, chromium oxide, ruthenium oxide, and any mixture thereof, wherein the metal oxide is present in a form having one or more surfaces, may be in a hydrated form, and wherein the gas mixture contacts at least one surface of the amorphous metal oxide during operation of the sensor;
         a pair of conductive electrodes operatively connected to a surface of the metal oxide; and
         an electrical device operatively connected to the pair of conductive electrodes, wherein the electrical device is capable of applying a constant potential or, alternatively, a constant current, between the pair of conductive electrodes and measuring a current or, alternatively, a potential, between the pair of conductive electrodes, from which a resistance can be derived as the gas mixture contacts the surface of the hydrated metal oxide to which the pair of conductive electrodes are operatively connected; and
   b. measuring the current or potential between the pair of conductive electrodes while the sensor is exposed to the gas mixture.

26. The method of claim 25 further comprising the step of calibrating the measured current or potential to the concentration of CO contained in the gas mixture.

27. The method of claim 25 wherein the sensor operates within a temperature range of from about 0° C. to about 300° C.

28. The method of claim 25 wherein the concentration of CO contained within a gas mixture is present at concentrations of from about 1 ppm to about 10,000 ppm.

29. A method for making a CO sensor comprising:
   a. operatively connecting a coating, substrate, or film of metal oxide to a pair of conductive electrodes, wherein the metal oxide is selected from the group consisting of iron oxide, cobalt oxide, vanadium oxide, chromium oxide, ruthenium oxide, and any mixture thereof; and
   b. operatively connecting an electrical device to the pair of conductive electrodes, wherein the electrical device is capable of applying a constant potential or, alternatively, a constant current, between the pair of conductive electrodes and measuring a current or, alternatively, a potential, between the pair of conductive electrodes, from which a resistance can be derived as a gas mixture contacts the surface of the coating, substrate, or film of hydrated metal oxide to which the pair of conductive electrodes are operatively connected.

30. A method for making a CO sensor, wherein the method comprises the steps of:
   a. combining $RuCl_3$ and NaOH to form a ruthenium oxide;
   b. dispersing the ruthenium oxide in water;
   c. spin coating the dispersion of ruthenium oxide onto a pair of inter-digitated conductive electrodes;
   d. removing the water to form a coating, substrate, or film of the ruthenium oxide operatively connected to the pair of inter-digitated conductive electrodes; and
   e. operatively connecting an electrical device to the pair of inter-digitated conductive electrodes, wherein the electrical device is capable of applying a constant potential or constant current between the pair of inter-digitated conductive electrodes and measuring a current or potential between the pair of inter-digitated conductive electrodes as a gas mixture contacts at least one surface of the hydrated ruthenium oxide.

* * * * *